(12) United States Patent
McKay

(10) Patent No.: US 8,801,793 B2
(45) Date of Patent: Aug. 12, 2014

(54) INTERBODY CONTAINMENT IMPLANT

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 595 days.

(21) Appl. No.: 13/008,426

(22) Filed: Jan. 18, 2011

(65) Prior Publication Data

US 2012/0185046 A1  Jul. 19, 2012

(51) Int. Cl.
*A61F 2/44* (2006.01)

(52) U.S. Cl.
USPC ............................ 623/17.16; 623/17.11

(58) Field of Classification Search
USPC ................. 623/17.11–17.16; 606/246
See application file for complete search history.

(56) References Cited

U.S. PATENT DOCUMENTS

| | | | |
|---|---|---|---|
| 4,997,432 A | 3/1991 | Keller | |
| 5,683,394 A | 11/1997 | Rinner | |
| 6,447,544 B1 * | 9/2002 | Michelson | 623/17.16 |
| 6,764,512 B2 | 7/2004 | Keller | |
| 7,192,447 B2 * | 3/2007 | Rhoda | 623/17.11 |
| 7,585,326 B2 | 9/2009 | de Villiers et al. | |
| 7,594,931 B2 | 9/2009 | Louis et al. | |
| 7,837,735 B2 | 11/2010 | Malone | |
| 7,850,734 B2 | 12/2010 | Oh et al. | |
| 8,579,980 B2 * | 11/2013 | DeLurio et al. | 623/17.15 |
| 2003/0191531 A1 * | 10/2003 | Berry et al. | 623/17.11 |
| 2004/0199254 A1 | 10/2004 | Louis et al. | |
| 2006/0142858 A1 * | 6/2006 | Colleran et al. | 623/17.11 |
| 2007/0162130 A1 | 7/2007 | Rashbaum et al. | |
| 2007/0179611 A1 | 8/2007 | DiPoto et al. | |
| 2008/0009946 A1 | 1/2008 | Douget et al. | |
| 2008/0215155 A1 | 9/2008 | de Villiers et al. | |
| 2008/0281424 A1 | 11/2008 | Parry et al. | |
| 2009/0093882 A1 | 4/2009 | Oh et al. | |
| 2009/0157186 A1 | 6/2009 | Magerl | |
| 2010/0106250 A1 | 4/2010 | Abdou | |

* cited by examiner

*Primary Examiner* — Nicholas Woodall
(74) *Attorney, Agent, or Firm* — Sorell Lenna & Schmidt LLP

(57) ABSTRACT

An interbody containment implant includes a body configured for delivery along a surgical pathway and disposed adjacent vertebrae. The body defines a cavity. At least one biologically compatible agent is configured for disposal within at least the cavity. A barrier is connected to the body and configured to be deployed to prevent the agent from migrating into the surgical pathway. Methods of use are disclosed.

14 Claims, 4 Drawing Sheets

INTERBODY CONTAINMENT IMPLANT

TECHNICAL FIELD

The present disclosure generally relates to medical devices, systems and methods for the treatment of musculoskeletal disorders, and more particularly to an implant system that contains at least one biologically compatible agent to enhance fixation with adjacent bone structures and for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Fusion and fixation treatments may employ implants such as interbody fusion devices to achieve arthrodesis. This disclosure describes an improvement over these prior art technologies.

SUMMARY OF THE INVENTION

Accordingly, an interbody containment implant system and method is provided that contains at least one biologically compatible agent for treating a vertebral column. It is contemplated that an implant of the system includes a body and a barrier to prevent the agent from undesirable migration. It is further contemplated that the implant system and method may be employed for an arthrodesis treatment.

In one particular embodiment, in accordance with the principles of the present disclosure, an interbody containment implant is provided. The interbody containment implant includes a body configured for delivery along a surgical pathway and disposed adjacent vertebrae. The body defines a cavity. At least one biologically compatible agent is configured for disposal within at least the cavity. A barrier is connected to the body and configured to be deployed to prevent the agent from migrating into the surgical pathway.

In one embodiment, the interbody containment implant includes a body configured for delivery along a surgical pathway and disposed adjacent vertebrae. The body being further configured for insertion within an intervertebral disc space and defining a cavity. At least one biologically compatible agent is configured for disposal within the cavity and/or adjacent the vertebrae. A barrier is connected to the body and slidably movable relative to the body. The barrier being configured to be slidably deployed after the body is inserted within the intervertebral disc space to prevent the agent from migrating into said surgical pathway.

In one embodiment, a method for treating vertebrae is provided. The method includes the steps of: providing an interbody implant, similar to those described; making an incision in a lateral portion of a patient; creating a surgical pathway extending from the incision into an intervertebral disc space of the patient; preparing the intervertebral disc space; delivering the body through the surgical pathway into the intervertebral disc space for treatment; and manipulating the barrier across the surgical pathway to prevent the agent from migrating into the surgical pathway.

BRIEF DESCRIPTION OF THE DRAWINGS

The present disclosure will become more readily apparent from the specific description accompanied by the following drawings, in which.

DETAILED DESCRIPTION OF THE INVENTION

Figure 1:
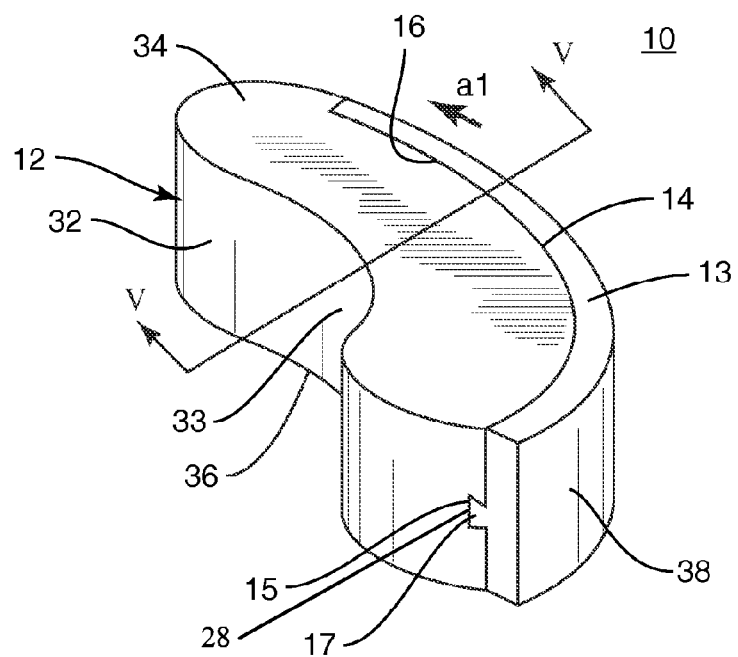
FIG. 1 is a perspective view of one particular embodiment of an interbody containment implant system in accordance with the principles of the present disclosure.

The exemplary embodiments of the interbody containment implant system and related methods of use disclosed are discussed in terms of medical devices for the treatment of musculoskeletal disorders and more particularly, in terms of an implant system that contains at least one biologically compatible agent and prevents material(s) from undesirable migration to treat a vertebral column. It is envisioned that the implant system includes an interbody cage implant having a barrier that blocks a surgical pathway after the cage has been implanted within a body of a patient. It is contemplated that the implant system is disposed to facilitate the fixation of opposing bone surfaces, such as, for example, bone surfaces disposed in an inferior/superior and/or an anterior/posterior configuration to maximize areas of engagement. It is further contemplated that the implant system may be deployed with the above configurations in a kidney-shaped geometry to utilize a sliding barrier.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed implant system may be alternatively employed in a surgical treatment with a patient in a prone or supine position, and/or employ various surgical approaches to the spine, including anterior, posterior, posterior mid-line, lateral, postero-lateral, medial, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

The following discussion includes a description of an interbody containment implant system and related methods of employing the interbody containment implant system in accordance with the principles of the present disclosure. Alternate embodiments are also disclosed. Reference will now be made in detail to the exemplary embodiments of the present disclosure, which are illustrated in the accompanying figures. Turning now to FIGS. 1-8, there is illustrated components of an interbody containment implant system including an interbody containment implant, such as, for example, a containment cage 10 in accordance with the principles of the present disclosure.

The components of the interbody containment implant system can be fabricated from materials suitable for medical applications, including metals, polymers, ceramics, biocompatible materials, bone materials and/or their composites, depending on the particular application and/or preference of a medical practitioner. For example, the components of the interbody containment implant system, individually or collectively, can be fabricated from materials such as stainless steel, titanium, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, biocompatible materials such as polymers including plastics, metals, ceramics and composites thereof, rigid polymers including polyphenylene, polyamide, polyimide, polyetherimide, polyethylene and epoxy, bone material including autograft, allograft, xenograft or transgenic cortical and/or corticocancellous bone, and tissue growth or differentiation factors, partially resorbable materials, such as, for example, composites of metals and calcium-based ceramics. Various components of the interbody containment implant system may have material composites, including the above materials, to achieve various desired characteristics such as strength, rigidity, elasticity, compliance, biomechanical performance, durability and radiolucency or imaging preference.

Cage 10 is configured for treating, for example, an affected section of a spine including vertebrae V, an intervertebral disc space I and body areas adjacent thereto. Cage 10 is configured for disposal within a spinal column and adjacent areas within a body of a patient, such as, for example, intervertebral disc space I between a first vertebrae $V_1$ and a second vertebrae $V_2$ of vertebrae V.

Cage 10 includes a body 12 having a generally kidney-shaped configuration for disposal with intervertebral disc space I. It is contemplated that the overall and/or cross-sectional geometry of body 12 may have various configurations, for example, round, oval, oblong, triangular, rectangular, polygonal, irregular, uniform, non-uniform, consistent or variable. Body 12 includes a cavity 11 defined within an interior space thereof. Cavity 11 is defined by an outer wall 30 of body 12 and has a similar kidney-shaped configuration. It is contemplated that cavity 11 may have various configurations, similar or alternative to outer wall 30, such as, for example, round, oval, oblong, triangular, rectangular, polygonal, irregular, uniform, non-uniform, consistent or variable. It is further contemplated that body 12 may include one or a plurality of cavities 11, which may be completely or partially separated by walls, screens and/or membranes.

Figure 6:
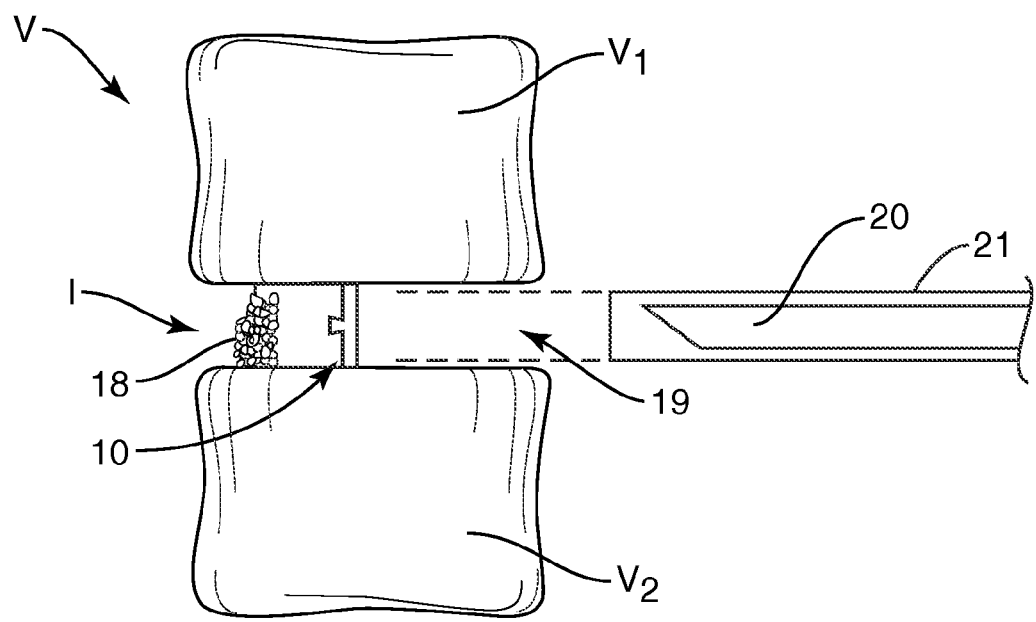
FIG. 6 is side view of the interbody containment implant system shown in FIG. 1 disposed with vertebrae.

Cavity 11 is configured for disposal of at least one biologically compatible agent, as described below, for surgical fusion and fixation applications of the interbody containment implant system. Other applications and procedures are also contemplated. Outer wall 30 may include one or a plurality of openings (not shown) for passage of the agent to body space and tissues adjacent vertebrae V (FIG. 6). It is contemplated that outer wall 30 may have alternative configurations, such as, for example, solid, porous, and/or include passages therethrough, and/or may include mesh or screens for passage of the agent therethrough.

Outer wall 30 defines an outer surface 32 that is substantially smooth for implantation within intervertebral disc space I. It is envisioned that all or only a portion of outer surface 32 may have alternate surface configurations, such as, for example, arcuate, undulating, rough, spiked, semi-porous, dimpled and/or polished, textured for friction fit and/or include fastening elements such as anchors, barbs, spikes, detents and/or openings.

Outer surface 32 includes a first planar surface 34 and an opposing second planar surface 36. Surfaces 34, 36 are configured for engagement with tissues corresponding to the endplates of vertebrae $V_1$, $V_2$. Outer surface 32 also includes an arcuate surface 14, which is convex and configured for connection to a barrier 13. Barrier 13 is attached to body 12 for slidable movement relative thereto to prevent undesired migration of the agent, as will be described. Outer surface also defines an opposing concave surface 33.

Figure 5:
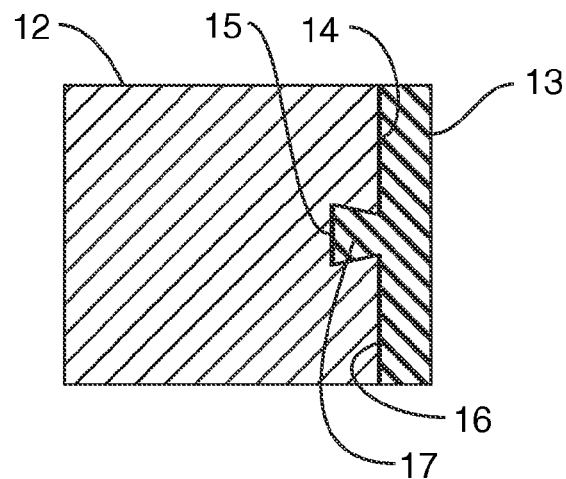
FIG. 5 is a cutaway cross sectional view of the body and the barrier of the interbody containment implant system taken along lines V-V shown in FIG. 1.

Barrier 13 has an arcuate configuration corresponding to the curvature of body 12. Barrier 13 includes a concave surface 16 relative to convex surface 14. Surface 16 is attached to surface 14 via a dovetail connection, as shown in FIG. 5. Surface 14 includes a channel 15 and surface 16 includes a protrusion 17. Protrusion 16 slidably mates with channel 15 and provides an interlock therebetween. Channel 15 is disposed along a longitudinal axis of body 12 in an arcuate orientation. Protrusion 16 is similarly disposed about a longitudinal axis along barrier 13 in an arcuate orientation. When mated, channel 15 and protrusion 16 allow barrier 13 to move in an arcuate trajectory with respect to body 12. It is contemplated that the curvature of channel 15 is substantially equal to the curvature of protrusion 16. It is further contemplated that the arc length of channel 15 is substantially equal to the arc length of protrusion 16.

The reciprocal convex/concave orientation of surfaces 14, 16 facilitates relative slidable movement of barrier 13 along an arcuate trajectory. It is contemplated that barrier 13 may be movable relative to body 12 in alternate trajectories or paths, such as, for example, linear, angled or alternate arcuate paths, and may project from alternate surfaces of body 12. It is further contemplated barrier 13 may be connected to body 12 with alternate configurations, such as, for example, multiple grooves/channels, adhesive, hinge and/or axial translation via threaded engagement.

Barrier 13 has an impermeable wall portion 38 to prevent the passage of one or more agents therethrough, as will be described. Wall portion 38 has a convex configuration. It is contemplated that all or only a portion of barrier 13 has an impermeable configuration, and that portions of barrier 13 may be agent permeable and include perforation, mesh and/or openings, according to the requirements of a particular application. Barrier 13 has a generally rectangular configuration to facilitate implantation within intervertebral disc space I. It is contemplated that barrier 13 may have various configurations, such as, for example, round, oval, oblong, triangular, rectangular, polygonal, irregular, uniform, non-uniform, consistent or variable.

Figure 2:
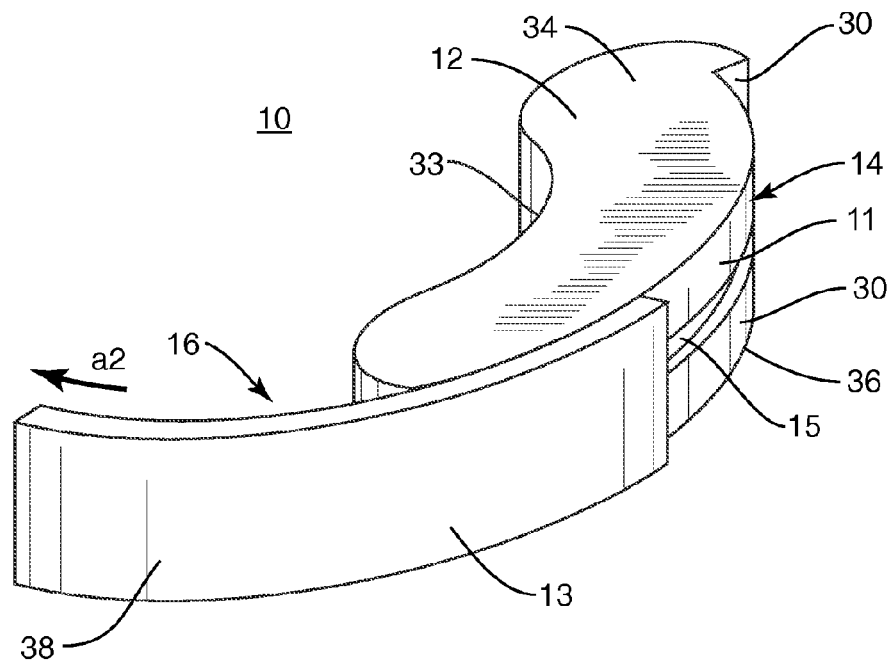
FIG. 2 is a perspective view of the interbody containment implant system shown in FIG. 1.
Figure 3:
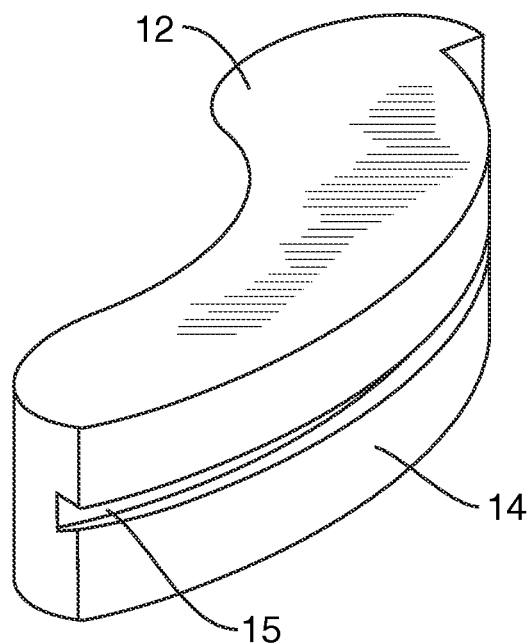
FIG. 3 is a cutaway perspective view of a body of the interbody containment implant system shown in FIG. 1.
Figure 4:
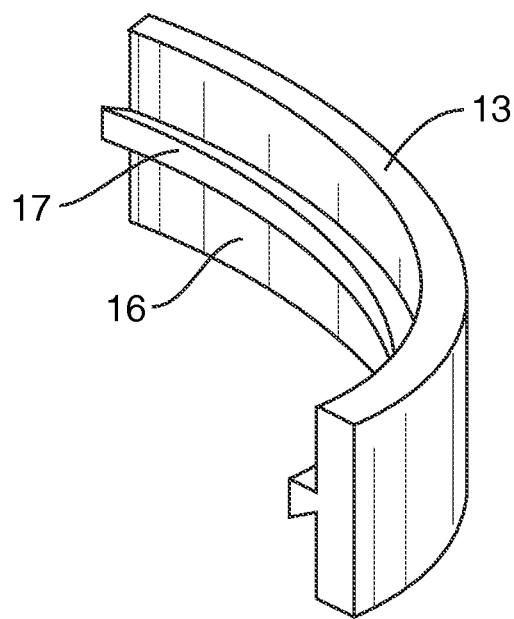
FIG. 4 is a cutaway perspective view of a barrier of the interbody containment implant system shown in FIG. 1.

In operation, barrier 13 is slidable between a retracted position (FIG. 1) and an extended or deployed position (FIG. 2). Barrier 13 is manipulable to the retracted position, as shown by arrow a1 in FIG. 1, and is manipulable to the extended position, as shown by arrow a2 in FIG. 2. It is envisioned that barrier 13 can be variably disposed between the retracted position and the extended position, depending on the particular application. It is further envisioned that channel 15 and/or protrusion 16 may movement enhancing features, such as, for example, lubricants. It is contemplated that relative movement of barrier 13 relative to body 12 may be intermittently locked via a ratchet configuration.

In assembly, operation and use, the interbody containment implant system is employed with a surgical procedure, such as, a fusion treatment of a spine of a patient including vertebrae V, intervertebral disc space I and body areas adjacent thereto, as discussed herein. Cage 10 may also be employed with other surgical procedures, such as, for example, discectomy, laminotomy, laminectomy, nerve root retraction, foramenotomy, facetectomy, decompression, spinal nucleus or disc replacement.

For example, cage 10 can be employed with a surgical arthrodesis procedure, such as, for example, fusion for treatment of an applicable condition or injury of an affected section of a spinal column and adjacent areas within a body, such as, for example, intervertebral disc space I between first vertebrae $V_1$ and second vertebrae $V_2$ of vertebrae V. It is contemplated that cage 10 can be inserted with intervertebral disc space I to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. It is envisioned that cage 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Cage 10 is then employed to augment the surgical treatment. Cage 10 can be delivered or implanted as a pre-assembled device or can be assembled in situ. Cage 10 can be completely or partially revised, removed or replaced in situ. It is contemplated that one or all of the components of cage 10 can be delivered to the surgical site via manual manipulation and/or a free hand technique. It is further contemplated that cage 10 may be inserted posteriorly, and then manipulated anteriorly and/or lateral and/or medial.

Figure 7:
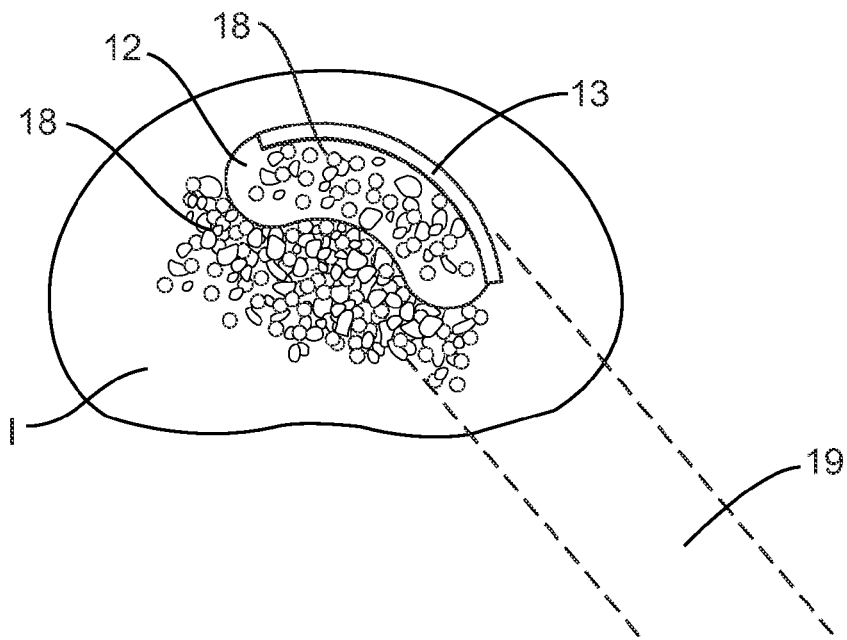
FIG. 7 is a plan view of the interbody containment implant system shown in FIG. 1 disposed with vertebrae.
Figure 8:
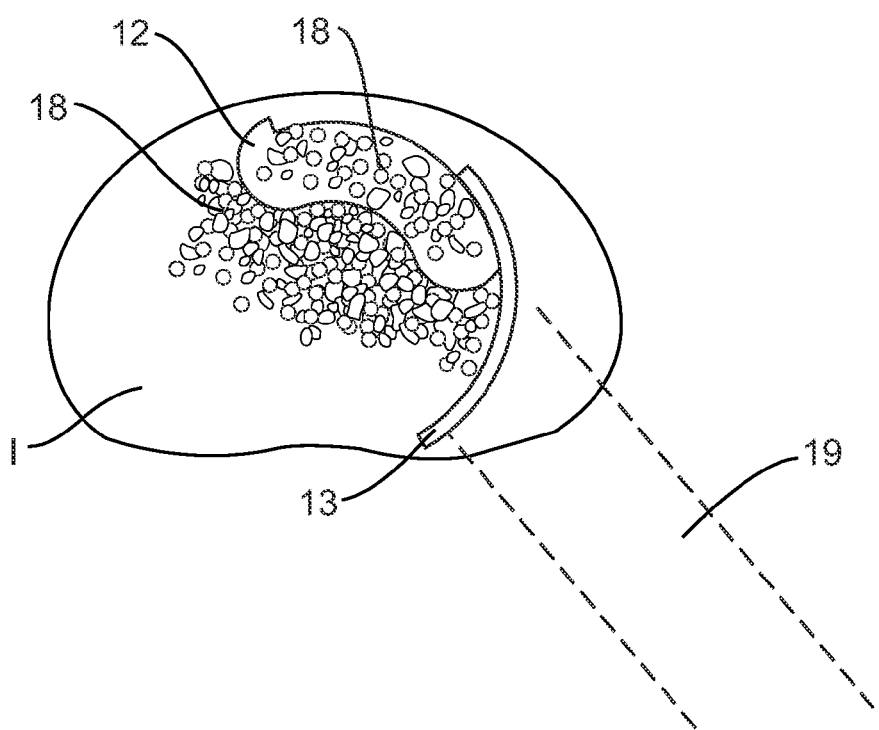
FIG. 8 is a plan view of the interbody containment implant system shown in FIG. 1 disposed with vertebrae.

During the surgical procedure, a sleeve 21 can be used to access intervertebral disc space I, as shown in FIGS. 6-8. A cutting instrument 20 creates a surgical pathway 19 for implantation of cage 10. A preparation instrument (not shown) can be inserted within sleeve 21 and disposed within intervertebral disc space I. The preparation instrument(s) can be employed to remove some or all disc tissue and fluids, adjacent tissues and/or bone, corticate, scrape and/or remove tissue from the surfaces of endplates of opposing vertebrae, as well as for aspiration and irrigation of the region according to the requirements of a particular surgical application.

Cage 10 is delivered through surgical pathway 19 into intervertebral disc space I with a delivery instrument (not shown) including a driver (not shown) via sleeve 21 for arthrodesis treatment. It is envisioned that cage 10 may be delivered along various surgical approaches to the spine, including anterior, posterior, posterior mid-line, lateral, postero-lateral, medial or antero-lateral and/or at various angular orientations. For example, in one embodiment, cage 10 is delivered along a surgical pathway that is disposed at an angle approximately 30 degrees from an axis transverse (as a vertical line through intervertebral disc space I in FIGS. 7-8) to a longitudinal axis of the spine. The driver delivers cage 10 into the prepared intervertebral disc space I, between vertebrae $V_1$ and vertebrae $V_2$, according to the requirements of a particular surgical application. Cage 10 is manipulated such that opposing surfaces 34, 36 engage endplates of opposing vertebrae $V_1$, $V_2$. A biologically compatible agent 18 is disposed within cavity 11 of body 12 prior to implantation of body 12 with intervertebral disc space I. Agent 18 is also delivered through sleeve 21 into intervertebral disc space I adjacent cage 10. It is envisioned that cavity 11 may be an empty or evacuated space for implantation and then agent 18 can be inserted through sleeve 21 and into body 12 through one or more openings (not shown) defined thereby.

Upon implantation of cage 10, barrier 13 is disposed in the retracted position, as shown in FIG. 7 and described above. After positioning of cage 10 and disposal of agent 18 within intervertebral disc space I, according to the requirements of a particular application, barrier 13 is manipulated to the extended position, as shown in FIG. 8 and described above, to create a barrier across surgical pathway 19 thus preventing agent 18 from migrating and/or escaping through surgical pathway 19. As such, the configuration of extended barrier 13 blocking surgical pathway 19 prevents agent 18 from passing into unwanted anatomical areas adjacent vertebrae V. The components of the interbody containment implant system secure, stabilize and immobilize vertebrae V in connection with the fusion procedure while preventing undesired migration of agent 18. It is envisioned that one or a plurality of cages 10 may be used for a surgical procedure employing the interbody containment implant system.

Cage 10 includes agent 18, such as, for example, bone growth promoting material, which may be disposed, packed or layered within, on or about the components and/or surfaces of cage 10 and may be disposed with openings found therein. The bone growth promoting material, such as, for example, bone graft can be a particulate material, which may include an osteoconductive material such as hydroxyapatite and/or an osteoinductive agent such as a bone morphogenic protein to enhance bony fixation of cage 10 with the adjacent vertebrae V.

It is contemplated that the bone graft may include therapeutic polynucleotides or polypeptides, which can be packed or otherwise disposed in, on or about the components and/or surfaces of cage 10. It is further contemplated that the bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, bone morphogenic protein (BMP), Growth and Differentiation Factors proteins (GDF) and cytokines. In one embodiment, cage 10 may be fabricated from allograft bone material.

It is contemplated that cage 10 may be coated with an osteoconductive material such as hydroxyapatite and/or osteoinductive agent such as BMP for enhanced bony fixation to the treated area. Cage 10 can be made of radiolucent materials such as polymers. Radiomarkers may be included for identification under x-ray, fluoroscopy, CT or other imaging techniques.

Cage 10 may include one or a plurality of agent reservoirs including agent(s) 18. The agent reservoirs can be configured as drug depots with medication for pain and may include antibiotics and/or therapeutics. It is envisioned that the agent reservoirs contain active agents and may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

Agent 18 may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

Agent 18 may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

Agent 18 may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

Although various embodiments are disclosed herein, other embodiments are contemplated. For example, in one embodiment, body 12 may include a cutout section that is fitted with barrier 13 therein. In one embodiment, barrier 13 is configured as a plate and can be mounted onto surface 14 without the cutout section. In one embodiment, barrier 13 can be separate from body 12, for example, barrier 13 can be attached to body 12 in situ after body 12 is inserted within the tissue and then manipulated across surgical pathway 19 and/or barrier 13 can be attached with a screw or snap-in mechanism.

In one embodiment, similar to cage 10 described above, a biasing element is mounted and/or formed with body 12 or barrier 13 to deploy barrier 13 into the extended position, as described above. In one embodiment, the biasing element is a spring (not shown), which is mounted within channel 15 and extending from outer wall 30. The spring engages a side surface of barrier 13 to bias barrier 13 to the extended position to prevent the agent from migrating into the surgical pathway, as described above. This spring loaded configuration can be used to provide a resilient force to assist in maneuvering barrier 13 into the extended position and the spring can be positioned on any of the various surfaces of cage 10 such that the spring can engage body 12 and barrier 13. It is contemplated that the spring may be mounted with barrier 13, for example, within or extending from protrusion 17 to engage outer wall 30.

In one embodiment, similar to cage 10 described above, a biasing element 28 is mounted and/or formed with body 12 or barrier 13 to deploy barrier 13 into the extended position, as described above. In one embodiment, biasing element 28 is a spring (not shown), which is mounted within channel 15 and extending from outer wall 30. The spring engages a side surface of barrier 13 to bias barrier 13 to the extended position to prevent the agent from migrating into the surgical pathway, as described above. This spring loaded configuration can be used to provide a resilient force to assist in maneuvering barrier 13 into the extended position and the spring can be positioned on any of the various surfaces of cage 10 such that the spring can engage body 12 and barrier 13. It is contemplated that the spring may be mounted with barrier 13, for example, within or extending from protrusion 17 to engage outer wall 30.

In one embodiment, similar to cage 10 described above, barrier 13 can adjustably click or lock into one or more deployment position(s). For example, as barrier 13 is moved from its retracted position to its extended position, surface 14 includes a saw-toothed rack that engages with a locking member or protrusion on barrier 13. Engagement of the protrusion with the rack allows barrier 13 to be selectively adjusted to a particular position relative to body 12. The engagement also prevents barrier 13 from moving back toward its retracted position and/or points between the retracted position and the extended position.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. An interbody containment implant comprising:
a body configured for delivery along a surgical pathway and disposed adjacent vertebrae, the body defining a cavity;
at least one biologically compatible agent configured for disposal within at least the cavity;

a barrier connected to said body and configured to be deployed to prevent the agent from migrating into said surgical pathway, the barrier not having a cavity configured for disposal of the at least one biologically compatible agent; and a biasing element mounted with the body or the barrier configured to deploy the barrier.

2. The interbody containment implant according to claim 1, wherein the at least one biologically compatible agent is bone growth promoting material.

3. The interbody containment implant according to claim 1, wherein the body defines an outer surface, the outer surface including a first portion configured to engage a first bone surface and a second portion configured to engage a second opposing bone surface.

4. The interbody containment implant according to claim 3, wherein the first bone surface is a lower endplate of a superior vertebrae and the second bone surface is an upper endplate of an inferior vertebrae.

5. The interbody containment implant according to claim 1, wherein the body has a kidney-shaped configuration.

6. The interbody containment implant according to claim 5, wherein a convex side of said kidney-shaped body includes a channel disposed about a longitudinal axis of said body and a concave side of said barrier includes a protrusion disposed about a longitudinal axis of said barrier and configured to slidably mate with said channel.

7. The interbody containment implant according to claim 1, wherein the biasing element including the barrier is fabricated from a shape memory material.

8. The interbody containment implant according to claim 1, wherein a convex surface of the barrier includes an impenetrable wall portion to prevent passage of the at least one biologically compatible agent therethrough.

9. An interbody containment implant, comprising:
a body configured for delivery along a surgical pathway and disposed adjacent vertebrae, the body being further configured for insertion within an intervertebral disc space and defining a cavity;

at least one biologically compatible agent configured for disposal within the cavity and/or adjacent the vertebrae;

a barrier connected to said body and being slidably movable relative to the body, the barrier being configured to be slidably deployed after the body is inserted within the intervertebral disc space to prevent the agent from migrating into said surgical pathway, wherein the barrier does not have a cavity configured for disposal of the at least one biologically compatible agent; and a biasing element mounted with the body or the barrier configured to deploy the barrier.

10. The interbody containment implant according to claim 9, wherein the agent is bone growth promoting material.

11. The interbody containment implant according to claim 9, wherein the body defines an outer surface, the outer surface including a first portion configured to engage a first bone surface and a second portion configured to engage a second opposing bone surface.

12. The interbody containment implant according to claim 11, wherein the first bone surface is a lower endplate of a superior vertebrae and the second bone surface is an upper endplate of an inferior vertebrae.

13. The interbody containment implant according to claim 9, wherein the biasing element including the barrier is fabricated from a shape memory material.

14. The interbody containment implant according to claim 9, wherein said barrier is attached to said body subsequent to said body being inserted within said tissue.

* * * * *